United States Patent
Woods et al.

[11] Patent Number: 5,811,425
[45] Date of Patent: Sep. 22, 1998

[54] HETEROCYCLIC COMPOUNDS AS COX-2 INHIBITORS

[75] Inventors: Keith W. Woods, Lake Forest; Richard W. McCroskey, Waukegan; Michael R. Michaelides, Highland Park, all of Ill.

[73] Assignee: Abbott Laboratories, Abbott Park, Ill.

[21] Appl. No.: 812,096

[22] Filed: Mar. 4, 1997

[51] Int. Cl.$^6$ .................. C07D 403/06; C07D 403/14; A61K 31/495; A61K 31/44
[52] U.S. Cl. .................. 514/249; 514/339; 514/365; 548/181; 546/270.4; 544/253
[58] Field of Search .................... 514/249, 339, 514/365; 548/181; 546/270.4; 544/253

[56] References Cited

U.S. PATENT DOCUMENTS

| | | | |
|---|---|---|---|
| 3,749,731 | 7/1973 | Zinnes et al. | 260/306 |
| 3,752,893 | 8/1973 | Roscoe et al. | 424/270 |
| 4,002,749 | 1/1977 | Rovnyak | 424/246 |
| 4,391,814 | 7/1983 | Vorbruggen | 424/272 |
| 4,618,617 | 10/1986 | Yamamoto | 514/364 |
| 4,963,689 | 10/1990 | Nagel et al. | 548/181 |
| 5,143,927 | 9/1992 | Boschelli et al. | 514/369 |
| 5,484,940 | 1/1996 | Grant et al. | 548/356.7 |

FOREIGN PATENT DOCUMENTS

| | | |
|---|---|---|
| 0530907 | 8/1992 | European Pat. Off. . |
| 0678508 | 8/1992 | European Pat. Off. . |
| 9009381 | 8/1990 | WIPO . |
| 9108744 | 6/1991 | WIPO . |
| 9419321 | 9/1994 | WIPO . |
| 9516687 | 6/1995 | WIPO . |

OTHER PUBLICATIONS

Chiarino et al; Synthesis and In Solution Behaviour of New 2–Substituted–4–Thiazolidinecarboxylic Acid Derivatives; J. Heterocyclic Chem., 26, 589 (1989).

*Primary Examiner*—Matthew V. Grumbling
*Attorney, Agent, or Firm*—Lawrence S. Pope

[57] ABSTRACT

The present invention relates to COX-2 inhibitors of the formula:

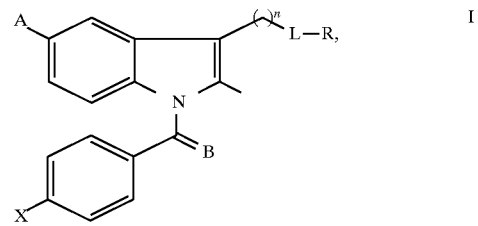

wherein,

A=halogen, $C_1$–$C_6$ alkyl, $SR^1$ or $OR^1$;

B=O, or H,H;

X=Br or Cl;

L=5-,6- or 7-membered heteroatom containing rings and is preferably a 5-membered heteroaromatics such as thiazole, oxazole, imidazole, or oxadiazole;

n=1–6, wherein the (C) is optionally branched;

R=optionally substituted aryl wherein aryl is selected from phenyl, pyridyl, naphthyl, benzothienyl, or quinoxolyl, alkyl, carboxyl, esters, amino, amide, or urea; and $R^1$=alkyl. The compounds are useful as research tools and could be useful as potential therapeutic agents in the inhibition of the PGHS-2 isozyme and in the treatment of inflammation in mammals including humans or other conditions associated with the production of prostaglandins.

7 Claims, No Drawings

HETEROCYCLIC COMPOUNDS AS COX-2 INHIBITORS

BACKGROUND OF THE INVENTION

The prostaglandins are potent biological compounds which produce a wide variety of biological effects. The discovery of two forms of prostaglandin endoperoxide H synthase-1 and -2 (PGHS-1 and -2) that catalyze the oxidation of arachidonic acid leading to prostaglandin biosynthesis has resulted in efforts to delineate the role of these isozymes. These isozymes have been shown to operate on two different prostaglandin biosynthesis pathways. The PGHS-1 pathway is expressed constitutively in most cell types. It responds to produce prostaglandins that regulate acute events in vascular homeostasis and also have a role in maintaining normal stomach and renal function. The newly discovered PGHS-2 pathway involves an induction mechanism which has been linked to inflammation, mitogenesis and ovulation phenomena.

Prostaglandin inhibitors provide therapy for pain, fever and inflammation, for example, in the treatment of rheumatoid arthritis and osteoarthritis. The non-steroidal antiinflammatory drugs (NSAIDs) such as ibuprofen, naproxen and fenamates inhibit both isozymes, i.e., PGHS-1 and PGHS-2. The inhibition of the constitutive enzyme PGHS-1 results in gastrointestinal side effects including ulcers and bleeding and incidence of renal problems with chronic therapy.

Thus, it is considered an advantage to provide compounds which inhibit the PGHS-2 pathway without inhibiting the PGHS-1 pathway to provide sufficient inflammation and pain relief without producing the negative side effects associated with inhibition of the PGHS-1 pathway. A general review of the current knowledge of PGHS-1 and PGHS-2 isozyme properties and a summary of inhibitors and their activity is provided in (1) Battistini, B.; Botting, R.; Bakhle, Y. S., "COX-1 and COX-2: Toward the Development of More Selective NSAIDs" Drug News and Perspectives, 7(8): 501–512 (1994); (2) DeWitt, D. L.; Bhattacharyya, D.; Lecomte, M.; Smith, W. L., "The Differential Susceptibility of Prostaglandin Endoperoxide H Synthases-1 and-2 to Nonsterodial Anti-inflammatory Drugs: Aspirin Derivatives as Selective Inhibitors:, Med. Chem. Res. 5(5): 325–343 (1995); and (3) Mitchell, J. A.; Larkin, S.; Williams, T. J., " Cycloxygenase-2: Regulation and Relevance in Inflammation. Biochem. Pharm 50(10): 1535–1542 (1995).

WO/91/08744 describes certain 4-hydroxythiazoles which are disclosed as lipoxygenase inhibitors. WO/95/16687 discloses certain indole compounds which are useful as platelet activating factor antagonists. WO/94/19321 describes certain inhibitors of HIV Reverse Transcriptase. D. Chiarino et al., in the Journal of Heterocyclic Chem. 26, 589–593 (1989), discloses the combination of L-cysteine with indomethacin to determine whether the amino acid could effectively deliver the non-steroidial anti-inflammatory drug ("NSAID").

The present invention is directed to selective inhibitors of the PGHS-2 pathway (via inhibition of the PGHS-2 isozyme) which are useful as research tools to provide information regarding the structure-activity relationship of compounds which selectively inhibit this isozyme. In addition, the compounds could be useful as potential therapeutic targets or drugs.

BRIEF SUMMARY OF THE INVENTION

The present invention encompasses a compound of the

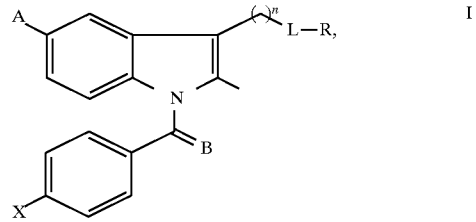

formula wherein,

A=halogen, $C_1$–$C_6$alkyl, halo$C_1$–$C_4$alkyl, $SR^1$ or $OR^1$;

B=O, or H,H;

X=Br or Cl;

L=a 5- to 7-membered heteroatom containing ring;

n=1–6, wherein the carbon is optionally branched;

R=
  (a) unsubstituted or mono- or multisubstituted aryl wherein aryl is selected from phenyl or naphthyl and the substituents are independently selected from halogen (Cl, Br, or F); $NO_2$, OH, $SO_2R^2$ wherein $R^2$ is $C_1$–$C_6$alkyl;
  (b) unsubstituted or mono- or multisubstituted heteroaryl wherein heteroaryl is selected from pyridyl, benzothienyl, or quinoxolyl and the substituents are independently selected from halogen (Cl, Br, or F); $NO_2$, OH, $SO_2R^2$ wherein $R^2$ is $C_1$–$C_6$alkyl;
  (c) $C_1$–$C_6$alkyl, $COOR^3$, $NR^4R^5$, $CONR^6R^7$, $NR^8(CO)NR^9R^{10}$ wherein $R^3$–$R^{10}$ are independently selected from H and $C_1$–$C_6$alkyl; and $R^1$=C1–C6alkyl or a pharmaceutically acceptable salt or prodrug thereof.

The compounds are useful as research tools as potent in vitro inhibitors of PGHS-2 isozyme and are useful as potential therapeutic agents in the inhibition of the PGHS-2 isozyme and in the treatment of inflammation in mammals including humans or other conditions associated with the production of prostaglandins even though initial in vivo data is not compelling. Thus, the present invention is also directed to pharmaceutical compositions containing the above PGHS-2 inhibitor as an active ingredient in a therapeutically effective or PGHS-2 inhibiting effective amount and a pharmaceutically acceptable excipient. In addition, the present invention is directed to a method of inhibiting prostaglandin biosynthesis in a host mammal comprising administering to a mammal in need of treatment thereof a pharmaceutically effective amount of a compound as recited herein.

DETAILED DESCRIPTION OF THE INVENTION

As used throughout the specification and the appended claims, the following terms have the meaning specified.

The term "alkyl" refers to a monovalent group derived from a straight or branched chain saturated C1–C6 hydrocarbon by the removal of a single hydrogen atom.

The term "aryl" refers to a mono- or bicyclic carbocyclic ring system comprising 6–12 carbon atoms and having one or two aromatic rings including, but not limited to, phenyl, naphthyl, tetrahydronaphthyl, indanyl, indenyl and the like. Aryl groups can be unsubstituted or substituted with one, two, three or four substituents independently selected from lower alkyl ($C_1$–$C_6$), halogen, halo$C_1$–$C_6$alkyl, $C_1$–$C_6$alkyloxy, $C_1$–$C_6$alkyloxycarbonyl, thio$C_1$–$C_6$alkyloxy, amino, $C_1$–$C_6$alkylamino, di$C_1$–$C_6$alkylamino, aminocarbonyl, mercapto, nitro, carboxylaldehyde, carboxy and hydroxy or other typical aromatic substituents.

The term "halo$C_1$–$C_4$alkyl" refers to branched or unbranched alkyl groups of one to four carbons which are substituted or multisubstituted with halogen atoms selected from C, Br or F.

The term "heteroaryl" refers to a mono- or bicyclic heteroaromatic ring system comprising 6–12 atoms including carbon atoms and heteroatoms and having one or two aromatic rings including, but not limited to, pyridyl, benzothienyl, quinoxyl, benzothiazole, quinoline, isoquinoline and benzoxazole. Heteroaryl groups can be unsubstituted or substituted at a carbon or appropriate heteroatom with those substituents as identified above for aryl.

The term "halogen" refers to —Cl, —F, —Br or I. The preferred halogen substituents are chosen from chlorine, fluorine or bromine.

The variable "L" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen atom and one sulfur atom; one nitrogen atom and one oxygen atom; two oxygen atoms in non-adjacent positions; one oxygen atom and one sulfur atom in non-adjacent positions; two sulfur atoms in adjacent positions; two sulfur atoms in adjacent positions and one nitrogen atom; and two adjacent nitrogen atoms and one sulfur atom; two non-adjacent nitrogen atoms and one oxygen atom. The 5-membered ring is the preferred group and has 0–2 double bonds wherein the nitrogen atoms, if present, can be quaternized. The preferred L groups are heteroaromatic and the preferred rings are chosen from thiazole, oxazole, imidazole or oxadiazole. The most preferred ring is thiazole.

The term "mammal" has its ordinary meaning and includes humans.

Asymmetric centers may exist in the compounds of the present invention and such compounds are comtemplated and included herein. Such compounds may be obtained from chiral starting materials or obtained through resolution of enantiomeric or diasteromeric mixtures by standard chromatographic means.

The present invention is directed to a compound of the formula:

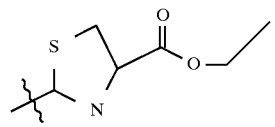

wherein,

A=halogen, $C_1$–$C_6$alkyl, halo$C_1$–$C_4$alkyl, $SR^1$ or $OR^1$;

B=O, or H,H;

X=Br or Cl;

L=a 5-, 6- or 7-membered ring containing one, two or three heteroatoms independently selected from nitrogen, sulfur or oxygen;

n=1–6, wherein the (C) is optionally branched;

R=
(a) unsubstituted or mono- or multisubstituted aryl wherein aryl is selected from phenyl or naphthyl and the substituents are independently selected from halogen (Cl, Br, or F); $NO_2$, OH, $SO_2R^2$ wherein $R^2$ is C1–C6alkyl;

(b) unsubstituted or mono- or multisubstituted heteroaryl wherein heteroaryl is selected from pyridyl, benzothienyl, or quinoxolyl and the substituents are independently selected from halogen (Cl, Br, or F); $NO_2$, OH, $SO_2R^2$ wherein $R^2$ is $C_1$–$C_6$alkyl;

(c) $C_1$–$C_6$alkyl, $COOR^3$, $NR^4R^5$, $CONR^6R^7$, $NR^8(CO)NR^9R^{10}$ wherein $R^3$–$R^{10}$ are independently selected from H and $C_1$–$C_6$alkyl; and $R^1$=$C_1$–$C_6$alkyl or a pharmaceutically acceptable salt or prodrug thereof with the proviso that a compound wherein A=—$OCH_3$, B=O, X=Cl, n=1

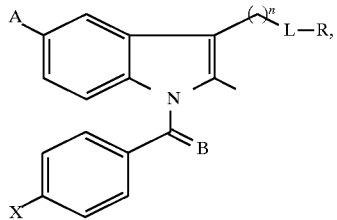

The compounds of the invention include those which are synthetically produced or those made by any other method including biological catabolism or metabolism. The present invention is further directed to a compound of formula II:

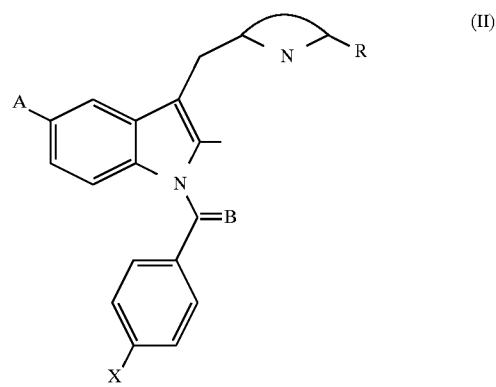

wherein,

A=halogen, $C_1$–$C_6$alkyl, halo$C_1$–$C_4$alkyl, $SR^1$ or $OR^1$;

B=O, or H,H;

X=Br or Cl;

R=
(a) unsubstituted or mono- or multisubstituted aryl wherein aryl is selected from phenyl or naphthyl and the substituents are independently selected from halogen (Cl, Br, or F); $NO_2$, OH, $SO_2R^2$ wherein $R^2$ is $C_1$–$C_6$alkyl;

(b) unsubstituted or mono- or multisubstituted heteroaryl wherein heteroaryl is selected from pyridyl, benzothienyl, or quinoxolyl and the substituents are independently selected from halogen (Cl, Br, or F); $NO_2$, OH, $SO_2R^2$ wherein $R^2$ is $C_1$–$C_6$alkyl;

(c) $C_1$–$C_6$alkyl, $COOR^3$, $NR^4R^5$, $CONR^6R^7$, $NR^8(CO)NR^9R^{10}$ wherein $R^3$–$R^{10}$ are independently selected from H and $C_1$–$C_6$alkyl; and $R^1$=$C_1$–$C_6$alkyl;

the group

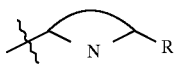

is selected from a moiety of the formula:

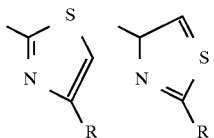

or a pharmaceutically acceptable salt or prodrug thereof.

In a preferred embodiment, the present invention is directed to a compound of the formula shown above wherein A is chosen from —OR$^1$ with all the remaining variables (X, B, L, R and n) remaining the same. The present invention is also directed to those compounds of formula I wherein L is selected from thiazole, oxazole, imidazole or oxadiazole with the remaining variables remaining the same as above.

The invention is also directed to a compound of formula I wherein R is chosen from groups (a) and (b) with the remaining variables remaining the same as above. The present invention is directed to a compound as described above wherein R is selected from unsubstituted or substituted phenyl, pyridyl, naphthyl, benzothienyl or quinoxolyl. The present invention is also directed to a compound as above, wherein, A is chosen from —OR$^1$ wherein R$^1$ is $C_1$–$C_3$ alkyl; B is selected from O or H,H; X is selected from Cl or Br; L is selected from thiazole; R is selected from p-Br-phenyl, difluorophenyl, naphthyl, m-Br-phenyl, p-Cl-phenyl, p-nitro-phenyl, benzothienyl, p-F-phenyl, p-SO$_2$CH$_3$. HCl-phenyl, m-nitro-phenyl, p-OH, m-nitro-phenyl, pyrid-3-yl, or pyrid-4-yl and n is chosen from 1 and to a compound as above wherein the compound is selected from, 3-(4-(4-bromophenyl)thiazol-2-ylmethyl)-1-(4-Chlorobenzoyl)-5-methoxy-2-methylindole;

1-(4-Chlorobenzoyl)-3-[4-(2,4-difluorophenyl)thiazol-2-ylmethyl]-5-methoxy-2-methylindole;

1-(4-Chlorobenzoyl)-5-methoxy-2-methyl-3-[4-(2-naphthyl)thiazol-2-ylmethyl]indole;

3-[4-(3-bromophenyl)thiazol-2-ylmethyl]-1-(4-Chlorobenzoyl)-5-methoxy-2-methylindole;

1-(4-Chlorobenzoyl)-3-[4-(4-Chlorophenyl)thiazol-2-ylmethyl]-5-methoxy-2-methylindole;

1-(4-Chlorobenzoyl)-5-methoxy-2-methyl-3-[4-(4-nitrophenyl)thiazol-2-ylmethyl]indole;

3-[4-(3-benzothienyl)thiazol-2-ylmethyl]-1-(4-Chlorobenzoyl)-5-methoxy-2-methylindole;

1-($^4$-Chlorobenzoyl)-3-[4-(4-fluorophenyl)thiazol-2-ylmethyl]-5-methoxy-2-methylindole;

1-($^4$-Chlorobenzoyl)-3-[4-(4-methanesulfonylphenyl)thiazol-2-ylmethyl]-5-methoxy-2-methylindole hydrobromide salt;

1-(4-Chlorobenzoyl)-5-methoxy-2-methyl-3-[4-(3-nitrophenyl)thiazol-2-ylmethyl]indole;

1-($^4$-Chlorobenzoyl)-3-[4-(4-hydroxy-3-nitrophenyl)thiazol-2-ylmethyl]-5-methoxy-2-methylindole;

1-(4-Chlorobenzoyl)-5-methoxy-2-methyl-3-[2-(3-pyridyl)thiazol-4-ylmethyl]indole;

1-(4-Chlorobenzoyl)-5-methoxy-2-methyl-3-[2-(4-pyridyl)thiazol-4-ylmethyl]indole;

1-(4-bromobenzyl)-3-[4-(4-Chlorophenyl)thiazol-2-ylmethyl]-5-methoxy-2-methylindole;

1-(4-bromobenzyl)-3-[4-(4-bromophenyl)thiazol-2-ylmethyl]-5-methoxy-2-methylindole; or 1-(4-bromobenzyl)-5-methoxy-2-methyl-3-[4-(4-nitrophenyl)thiazol-2-ylmethyl]indole or pharmaceutically acceptable salts or prodrugs thereof.

The preferred compounds are as listed above. As can be seen from the specific examples or compounds, the preferred point of attachment off the linking alkylene group of the indomethacin ring to group L is to a carbon atom on the heteroaryl ring and the R group is off the heteroatom containing or heteroaryl group L at the alpha carbon position adjacent to the lower heteroatom (e.g. Nitrogen atom as shown in the example structures). The point of attachment of the R group to the L moiety can be any non-substituted carbon atom on, for example, the aryl ring or additional R moiety.

The present invention is also directed to a method of inhibiting a PGHS-2 isozyme comprising administering a compound of formula I

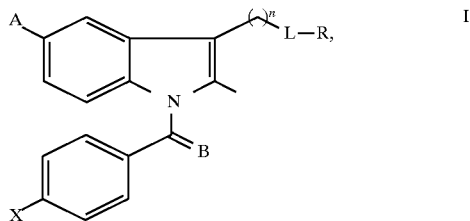

wherein,

A is selected from halogen, $C_1$–$C_6$alkyl, halo$C_1$–$C_4$alkyl, SR$^1$ or OR$^1$;

B is selected from O or H,H;

X is selected from Br or Cl;

L is selected from a 5-, 6- or 7-membered ring containing one, two or three heteroatoms independently selected from nitrogen, sulfur or oxygen;

n is selected from 1–6, wherein the carbon is optionally branched;

R is selected from
(a) unsubstituted or mono- or multi-substituted aryl wherein aryl is selected from phenyl or naphthyl and the substituents are independently selected from halogen (Cl, Br, or F); NO$_2$, OH, SO$_2$R$^2$ wherein R$^2$ is $C_1$–$C_6$alkyl;
(b) unsubstituted or mono- or multi-substituted heteroaryl wherein heteroaryl is selected from pyridyl, benzothienyl, or quinoxolyl and the substituents are independently selected from halogen (Cl, Br, or F); NO$_2$, OH, SO$_2$R$^2$ wherein R$^2$ is $C_1$–$C_6$alkyl;
(c) $C_1$–$C_6$alkyl, COOR$^3$, NR$^4$R$^5$, CONR$^6$R$^7$, NR$^8$(CO)NR$^9$R$^{10}$ wherein R$^3$–R$^{10}$ are independently selected from H and $C_1$–$C_6$alkyl; and R$^1$ is selected from $C_1$–$C_6$alkyl, or a pharmaceutically acceptable salt or prodrug thereof to a mammal wherein the compound selectively inhibits PGHS-2 isozyme relative to PGHS-1 isozyme.

The invention also relates to a method of inhibiting a PGHS-2 isozyme comprising administering a compound of formula II

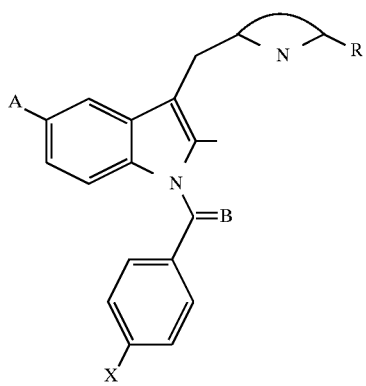

to a mammal, wherein
A=halogen, $C_1$–$C_6$alkyl, halo$C_1$–$C_4$alkyl, $SR^1$ or $OR^1$;
B=O, or HH;
X=Br or Cl;
R=
  (a) unsubstituted or mono- or multisubstituted aryl wherein aryl is selected from phenyl or naphthyl and the substituents are independently selected from halogen (Cl, Br, or F); $NO_2$, OH, $SO_2R^2$ wherein $R^2$ is $C_1$–$C_6$alkyl;
  (b) unsubstituted or mono- or multisubstituted heteroaryl wherein heteroaryl is selected from pyridyl, benzothienyl, or quinoxolyl and the substituents are independently selected from halogen (Cl, Br, or F); $NO_2$, OH, $SO_2R^2$ wherein $R^2$ is $C_1$–$C_6$alkyl;
  (c) $C_1$–$C_6$alkyl, $COOR^3$, $NR^4R^5$, $CONR^6R^7$, $NR^8(CO)NR^9R^{10}$ wherein $R^3$–$R^{10}$ are independently selected from H and $C_1$–$C_6$alkyl; and
$R^1$=$C_1$–$C_6$alkyl; and the group

is selected from a five-membered heteroaromatic ring containing 1, 2 or 3 heteroatoms chosen from N, O or S;
or a pharmaceutically acceptable salt or prodrug thereof and relates to the compounds of the above formula.

By pharmaceutically acceptable salt is meant those salts which are suitable for use in contact with the tissues of humans and other mammals or animals without undue toxicity, irritation, allergic response and the like. Pharmaceutically acceptable salts are well known in the art. For example, S. M. Berge, et al., describe pharmaceutically acceptable salts in detail in J. Pharmaceutical Sciences, 66:1–19 (1977). The salts can be prepared in situ during the final isolation and purification of the compounds of the invention, or separately by reacting the free base function (if present) with a suitable organic acid. Representative acid addition salts include acetate, adipate, alginate, ascorbate, aspartate, benzenesulfonate, benzoate, bisulfate, borate, butyrate, and other well known acid addition salts. Representative alkali or alkaline earth metal salts include sodium, lithium, potassium, calcium, magnesium, and the like as well as non-toxic ammonium, tetramethylammonium, tetraethylammonium, methylamine, dimethylamine, trimethylamine, triethylamine and the like.

The present invention also includes those compounds which, upon metabolic cleavage, yield the compounds of the invention. The term "metabolically cleavable group" or "metabolic cleavage" denotes a moiety which is readily cleaved in vivo from the compound bearing it wherein the compound, after cleavage, remains or becomes the pharmceutically active compound as claimed and recited herein. Metabolically cleavable groups are well known to those of ordinary skill in the art and include such groups as alkanoyl (acetyl, propionyl, butyryl and the like), unsubstituted and substituted aroyl (such as benzoyl and substituted benzoyl), alkoxycarbonyl (such as ethoxy carbonyl), trialkylsilyl (such as trimethyl- and triethylsilyl), monoesters formed with dicarboxylic acids (such as succinyl) and the like.

Because of the ease with which the metabolically cleavable groups of the compounds of the invention are cleaved in vivo, the compounds bearing such groups act as prodrugs of the prostaglandin biosynthesis inhibitors of the invention. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987.

The compounds of the invention are selective inhibitors of PGHS-2. As such, these compounds are useful as research tools and based on in vitro inhibition data potentially useful as therapeutic agents in the treatment of conditions which are mediated by PGHS-2 activity and which involve the production of prostaglandins and associated pathological conditions. Thus, the compounds are useful as potent in vitro inhibitors of PGHS-2 isozyme. Inhibition of this isozyme is associated with the treatment of acute inflammatory conditions (such as those resulting from infection) and chronic inflammatory conditions (such as those resulting from asthma, arthritis and inflammatory bowel disease). Inhbitors of PGHS-2 isozyme are also useful as analgesics and anti-pyretic agents.

Prostaglandin Inhibition Analysis
Recombinant Human PGHS-1 and -2 Enzyme Assays:

A compound of the invention was dissolved in DMSO (3.3%v/v) and preincubated with microsomes from recombinant human PGHS-1 and-2 expressed in the baculovirus/ Sf9 cell system (Gierse, J. K., Hauser, S. D., Creely, D. P., Koboldt, C., Rangwala, S. H., Isakson, P. C., and Siebert, K. "Expression and selection inhibition of the constitutive and inducible forms of cyclooxygenase", Biochem J. 305: 479 (1995)), together with the cofactors phenol (2 mM) and hematin (1 uM) for 60 minutes prior to the addition of 10 uM arachidonic acid. The reaction was allowed to run for 2.5 minutes at room temperature prior to quenching with HCl and neutralization with NaOH. $PGE_2$ production in the presence and absence of the drug was determined by Enzyme ImmunoAssay ("EIA") analysis as described below.

EIA Determination of Prostaglandins

EIA reagents for prostaglandin determination were purchased from Perspective Diagnostics, Cambridge, Mass. $PGE_2$ levels in lavage fluids were determined after the samples were dried under nitrogen and reconstituted with assay buffer. $PGE_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density measured using a microplate reader (Vmax, Molecular Devices Corp., Menlo Park, Calif.).

Carragennan Induced Pleurisy Test (CIP)

Inhibition of carragennan induced pleurisy in rats was determined essentially as described by F. B. De Brito, (Pleurisy and Pouch Models of Acute Inflammation in Pharmacological Methods in the Control of Inflammation, Eds, J. Y. Chang and A. J. Lewis, Alan Liss Inc., New York: 173–194 (1989) and Vinegar et al. ("Quantitative studies of the pathway to acute carrageenan inflammation", Fed. Proc., 35: 2447–2456 (1976)). Briefly, eight Sprague-Dawley rats were orally dosed with 10 mg/kg of a compound of the invention 30 minutes prior to intrapleural injection of lambda carrageenan (Sigma Chemical Col, St Louis Mo.). Four hours after carrageenan injection, the animals were euthanized and their pleural cavities lavaged with ice cold saline. The lavage fluid was then added to two volumes of ice cold methanol (final methanol concentration 66%) to lyse cells and precipitate protein. Prostaglandin levels in the methanol lavage fluid were then determined by EIA.

In Vitro and In Vivo Results

When tested in the recombinant human PGHS-1 and -2 enzyme assays as described above, all representative compounds were shown to be potent inhibitors of recombinant human PGHS-2 (Table 1). All representative compounds (examples) were selective inhibitors of PGHS-2 (COX-2) relative to PGHS-1 (COX-1).

TABLE 1

| Example | COX-1 (% inhib. @ 100 uM) | COX-2 IC$_{50}$ (nM) | CIP (inhibition @ 10 mg/kg) |
| --- | --- | --- | --- |
| 1 | 32 | 0.3 | 43% |
| 2 | 20 | 82% @ 100 nM | 16% |
| 3 | 21 | 7 | |
| 4 | 35 | 8 | 24% |
| 5 | 16 | 14 | |
| 6 | 26 | 12 | |
| 7 | 23 | 1 | 20% |
| 8 | 36 | 12 | |
| 9 | 40 | 60 | |
| 10 | 31 | 85% @ 100 nM | |
| 11 | 23 | 48% @ 100 nM | 30% |
| 12 | 40 | 20 | |
| 13 | 49 | 77% @ 100 nM | 14% |
| 14 | 15 | 7 | 36% |
| 15 | 15 | 30 | |
| 16 | 21 | 7 | 31% |

As also shown in Table 1, the in vivo results for the compounds indicated ranged from 14–43% inhibition, none of which are significantly potent but other in vivo screens could provide more significant results.

Pharmaceutical Compositions

The present invention is also directed to compositions which comprise compounds of the present invention formulated together with a pharmaceutically acceptable carrier. The pharmaceutical compositions may be specially formulated for oral administeration in solid or liquid form, for parenteral injection, or for rectal administration. The compositions of the invention may be administered to humans and other mammals or animals orally, rectally, parenterally, intracisternally, intravaginally, intraperitoneally, topically (as by powders, ointments, or drops), bucally, or as an oral or nasal spray. The term "parenteral" administration as used herein means modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

Compounds of the invention are prepared as shown in the examples section by Schemes 1–3. Indomethacin (1) or an analog thereof of the formula:

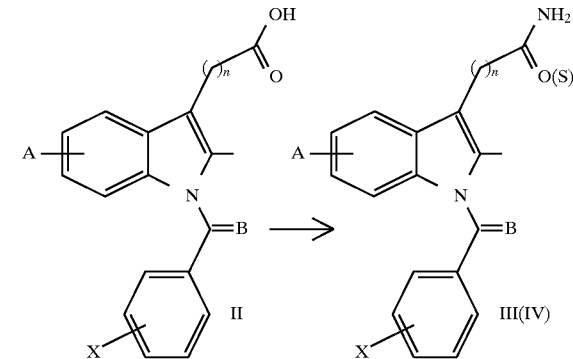

is reacted with an amidating reagent such as isobutylchloroformate/$NH_3$(g) in THF or other suitable aprotic solvent at about zero degrees to room temperature to form a compound of formula III which is then treated with a sulfur reagent such as $P_4S_{10}$ in a suitable solvent such as THF/dioxane (heated to refluxing) to form a sulfamide derivative of formula III (e.g., IV which is like formula 3 in the examples). The L group as recited in the claims and as shown herein is then formed by treating the sulfamide with a substituted two carbon fragment (alpha halo ketone or X—C—C(O)R with X=Cl or Br) to form, upon ring closure, an R substituted thiazole ring (shown as compound 4 in scheme 1 for the indomethacin product) which is within the scope of the invention. The R group on the two carbon fragment can be varied to provide, after ring formation, the multitude of aryl or heteroaryl substituents off the L-group (e.g. —L—R) as claimed herein. Alternatively, the heterocyclic system (L moiety) can be built off indomethacin or an analog thereof by forming an alpha halo ketone from the carboxlic acid precursor (II) as shown below.

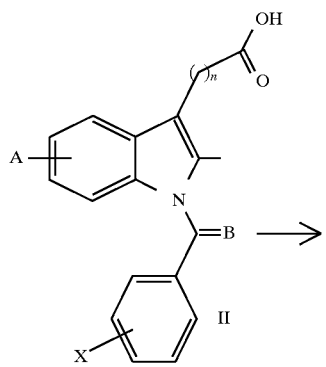

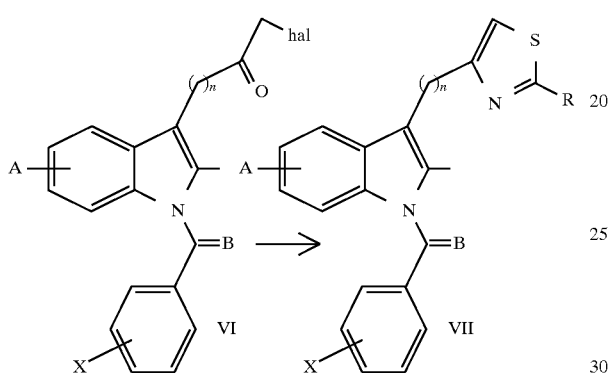

In the above case, a substituted thio amide as specifically shown in Scheme II is utilized as the R-containing fragment (e.g. pyridyl) which serves to build the L moiety by reacting with a halo methyl ketone. Indomethacin or an analog thereof is treated with a halogenating agent to form an acid halide which is then alkylated to form, after treatment with H-hal, the halomethyl ketone (VI). The reaction conditions require heat in a suitable solvent such as THF/CH$_2$Cl$_2$ or equivalent solvent or solvent blend. Alternatively, and for B equal to H, H (C=B is —CH$_2$—), an indomethacin analog (II with B as H,H), may be prepared from an indole acetic acid intermediate as shown in Scheme III. In essence, a substituted benzyl halide is reacted with the alkyl ester of the indole acetic acid to form an indomethacin alkyl ester analog which is then amidated to form a compound such as compound 11 in Scheme III. This is further manipulated as described above or as shown in Scheme III to form a compound of formula I as claimed herein.

EXAMPLES

The following compounds as presented in Table 2 and as further followed by the detailed preparation of the examples are compounds of the invention that are useful as COX-2 inhibitors. In the Table, n is 1. These compounds are readily prepared from commercially available starting materials or from readily prepared starting materials as described herein or below.

TABLE 2

| L | R | A(OR$^1$) | B | X | R1 |
|---|---|---|---|---|---|
| (thiazole) | 4-Br-phenyl | OCH$_3$ | O | Cl | CH$_3$ |
| " | 2,4-F$_2$-phenyl | " | " | " | " |
| " | naphthyl | " | " | " | " |
| " | 3-Br-phenyl | " | " | " | " |
| " | 4-Cl-phenyl | " | " | " | " |
| " | 4-NO$_2$-phenyl | " | " | " | " |

TABLE 2-continued
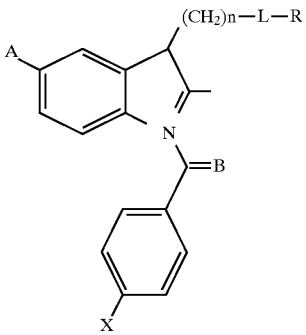
| L | R | A(OR¹) | B | X | R1 |
|---|---|---|---|---|---|
| " | 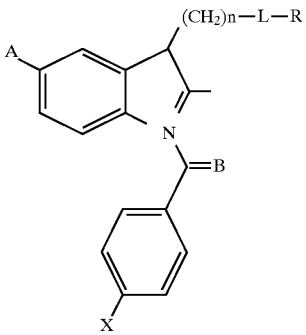 | " | " | " | " |
| " | 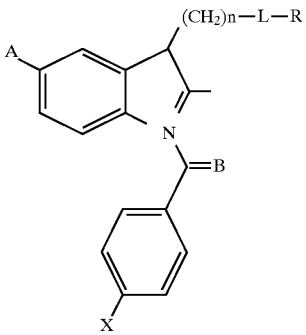 | " | " | " | " |
| " | 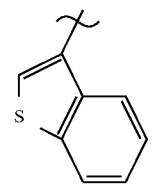 | " | " | " | " |
| " | 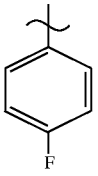 | " | " | " | " |
| " | 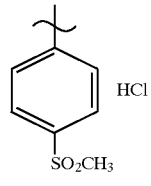 | " | " | " | " |
| 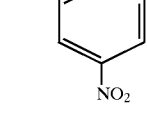 | 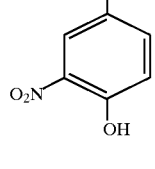 | " | " | " | " |
| " | 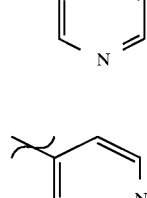 | " | " | " | " |
TABLE 2-continued
| L | R | A(OR¹) | B | X | R1 |
|---|---|---|---|---|---|
| 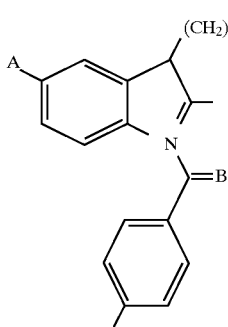 | 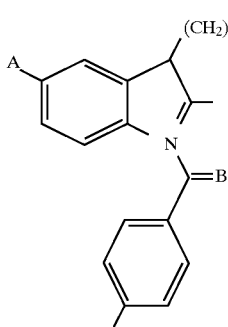 | " | H, H | 4-Br | CH₃ |
| " | 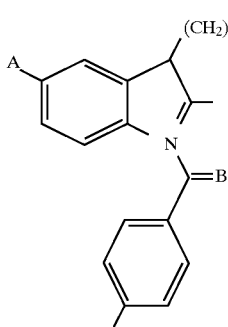 | " | " | " | " |
| " | 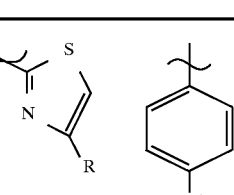 | " | " | " | " |
Scheme I
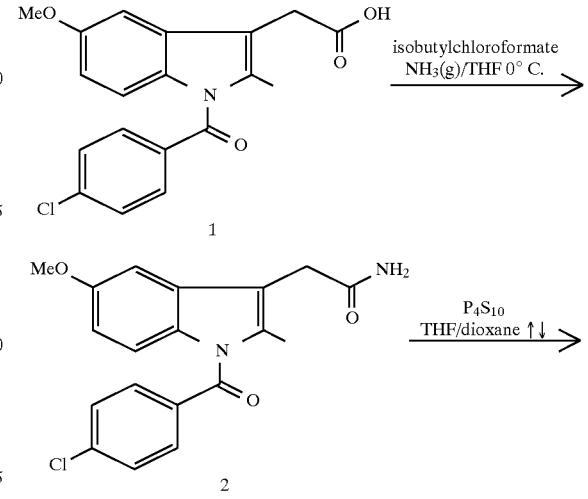

-continued
Scheme I

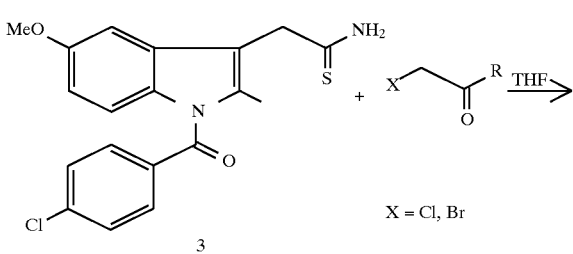

X = Cl, Br

3

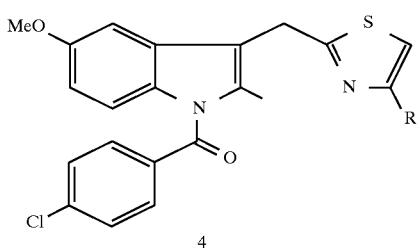

4

Example 1:

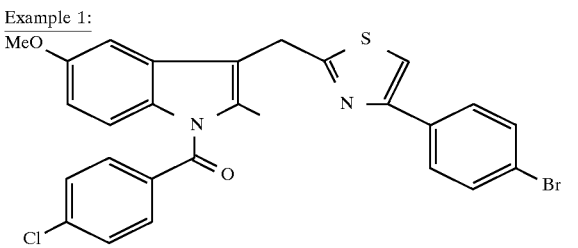

Step 1

1-(4-chlorobenzoyl)-5-methoxy-2-methylindole-3 acetamide (2).

Indomethacin (10 g; 0.028 mol) in 150 mL THF was treated with triethylamine (4.8 mL; 0.035 mol) and cooled to −10° C. Isobutylchloroformate (4.4 mL; 0.033 mol) was added and the reaction was stirred at −10° C. for 10 min. The ice bath was removed and $NH_3$ was bubbled through the solution for 15 min. The resulting pale yellow solid was collected, slurried in $CH_2Cl_2$ and filtered again. The product was used with no further purification.

Step 2

1-(4-Chlorobenzoyl)-5-methoxy-2-methylindole-3-thioacetamide (3).

The amide from step one (9.5 g; 0.0266 mol) was dissolved in 30 mL THF and 9 mL p-dioxane. $P_4S_{10}$ (3.9 g; 0.009 mol) was added and the reaction was heated at reflux overnight. The solvent was evaporated and the residue was slurried in acetone. The solids were collected and used with no further purification.

Step 3

3-[4-(4-bromophenyl)thiazol-2-ylmethyl]-1-(4-Chlorobenzoyl)-5-methoxy-2-methylindole.

The thioamide from step 2 (400 mg; 1.07 mmol) and 2,4'-dibromoacetophenone (370 mg; 1.33 mmol) in 10 mL THF were stirred at room temperature overnight. The reaction was diluted with EtOAc and washed successively with saturated $NaHCO_3$ (2×), water (1×) and brine (1×), dried over $MgSO_4$ and evaporated. The product was recrystallized from EtOAc to give 250 mg (42%) of an off white solid. m.p. 177°–180° C. $^1H$ NMR (DMSO-$d_6$) δ: 2.35 (s, 3H), 3.75 (s, 3H), 4.5 (s, 2H), 6.7 (dd, J=3Hz, J=12Hz, 1H), 6.9 (d, J=9Hz, 1H) 7.19 (d, J=3Hz, 1H), 7.6–7.75 (m, 7H), 7.9 (d, J=9Hz, 2H), 8.0 (s, 1H); MS: (DCI) (M+H)$^+$ m/z=553. Anal. Calcd for $C_{27}H_{20}BrClN_2O_2S$: C, 58.76; H, 3.65; N, 5.07. Found: C, 57.96; H, 3.64; N, 4.81.

Example 2

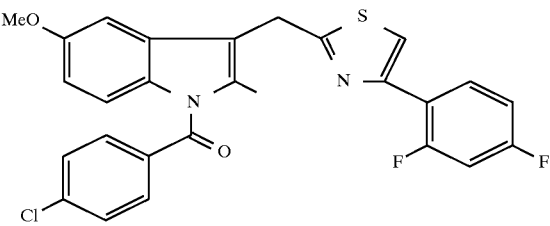

1-(4-Chlorobenzoyl)-3-[4-(2,4-difluorophenyl) thiazol-2-ylmethyl]-5-methoxy-2-methylindole.

The product was prepared according to the procedure for example 1 substituting 2-bromo-2',4'-difluoroacetophenone for 2,4'-dibromoacetophenone in step 3. m.p. 134°–136° C. $^1H$ NMR (DMSO-$d_6$) δ: 2.35 (s, 3H), 3.75 (s, 3H), 4.5 (s, 2H), 6.7 (dd, J=12Hz, J=3Hz, 1H), 6.9 (d, J=9Hz, 1H) 7.19 (d, J=3Hz, 1H), 7.2–7.3 (m, 1H), 7.35–7.41 (m, 1H), 7.4–7.5 (m, 4H), 7.8 (d, J=3Hz, 1H), 8.15–8.21 (m, 1H); MS: (DCI) (M+H)$^+$511. Anal. Calcd for $C_{27}H_{19}ClF_2N_2O_2S$: C, 63.71; H, 3.76; N, 5.50. Found: C, 63.67; H, 3.65; N, 5.44.

Example 3

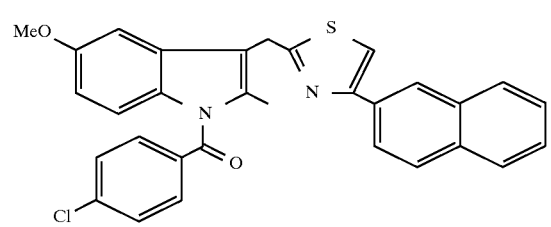

1-(4-Chlorobenzoyl)-5-methoxy-2-methyl-3-[4-(2-naphthyl)thiazol-2-ylmethyl]indole.

The product was prepared according to the procedure for example 1 substituting 2-bromo-2'-acetonaphthone for 2,4'-dibromoacetophenone in step 3. mp 131°–133° C. $^1H$ NMR (DMSO-$d_6$) δ: 2.35 (s, 3H), 3.75 (s, 3H), 4.5 (s, 2H), 6.7 (dd, J=12Hz, J=3Hz, 1H), 6.9 (d, J=9Hz, 1H) 7.19 (d, J=3Hz, 1H), 7.3–7.75 (m, 6H), 7.9–8.1 (m, 5H), 8.6 (s, 1H); MS: (DCI) (M+H)$_+$ m/z=523. Anal. Calcd for $C_{31}H_{23}ClN_2O_2S$: C, 71.19; H, 4.43; N, 5.36. Found: C, 70.92; H, 4.27; N, 5.16.

Example 4

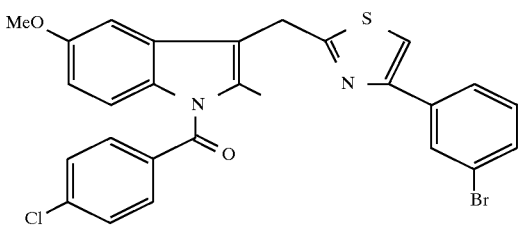

3-[4-(3-bromophenyl)thiazol-2-ylmethyl]-1-(4-Chlorobenzoyl)-5-methoxy-2-methylindole.

The product was prepared according to the procedure for example 1 substituting 2,3'-dibromoacetophenone for 2,4'-dibromoacetophenone in step 3. mp 208°–212° C. $^1$H NMR (DMSO-$d_6$) δ: 2.35 (s, 3H), 3.75 (s, 3H), 4.5 (s, 2H), 6.7 (dd, J=12Hz, J=3Hz, 1H), 6.9 (d, J=9Hz, 1H) 7.19 (d, J=3Hz, 1H), 7.4 (t, J=9Hz, 1H), 7.5 (m, 1H), 7.5 (m, 4H), 7.9 (m, 1H), 8.1 (s, 1H), 8.2 (t, J=9Hz, 1H); MS: (DCI) (M+H)$^+$ m/z=553. Anal. Calcd for $C_{27}H_{20}BrClN_2O_2S \cdot 0.75$ HBr: C, 52.94; H, 3.41; N, 4.57. Found: C, 53.26; H, 2.95; N, 4.56.

Example 5

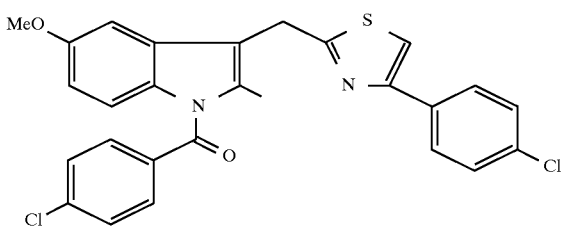

1-(4-Chlorobenzoyl)-3-[4-(4-Chlorophenyl)thiazol-2-ylmethyl]-5-methoxy-2-methylindole.

The product was prepared according to the procedure for example 1 substituting 2-bromo-4'-Chloroacetophenone for 2,4'-dibromoacetophenone in step 3. m.p. 186°–188° C. $^1$H NMR (DMSO-$d_6$) δ: 2.35 (s, 3H), 3.75 (s, 3H), 4.5 (s, 2H), 6.7 (dd, J=12Hz, J=3Hz, 1H), 6.9 (d, J=9Hz, 1H) 7.19 (d, J=3Hz, 1H), 7.5 (d, J=9Hz, 2H), 7.45–7.55 (m, 4H), 7.9–8.0 (m, 3H); MS: (DCI) (M+H)$^+$ m/z=507. Anal. Calcd for $C_{27}H_{20}Cl_2N_2O_2S$: C, 63.90; H, 3.97; N, 5.52. Found: C, 63.91; H, 3.86; N, 5.37.

Example 6

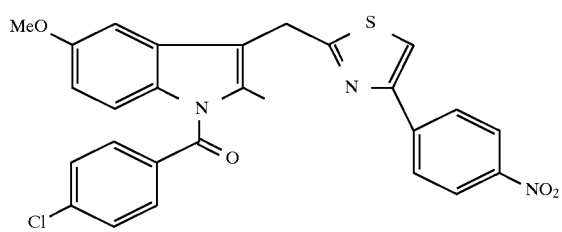

1-(4-Chlorobenzoyl)-5-methoxy-2-methyl-3-[4-(4-nitrophenyl)thiazol-2-ylmethyl]indole.

The product was prepared according to the procedure for example 1 substituting 2-bromo-4'-nitroacetophenone for 2,4'-dibromoacetophenone in step 3. m.p. 219° C. with decomposition. $^1$H NMR (DMSO-$d_6$) δ: 2.35 (s, 3H), 3.75 (s, 3H), 4.55 (s, 2H), 6.7 (dd, J=12Hz, J=3Hz, 1H), 6.9 (t, J=9Hz, 1H) 7.19 (d, J=3Hz, 1H), 7.45–7.55 (m, 4H), 8.2–8.38 (m, 5H); MS: (DCI) (M+H)$^+$ m/z=518.

Example 7

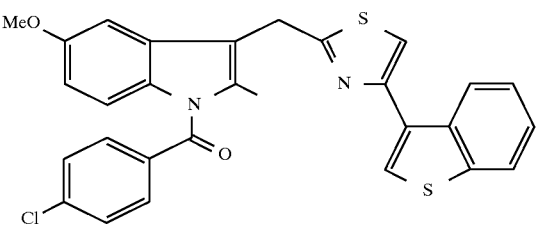

3-[4-(3-benzothienyl)thiazol-2-ylmethyl]-1-(4-Chlorobenzoyl)-5-methoxy-2-methylindole.

The product was prepared according to the procedure for example 1 substituting 3-Chloroacetylbenzo-[b]thiophene for 2,4'-dibromoacetophenone in step 3. m.p. 68°–72° C. $^1$H NMR (DMSO-$d_6$) δ: 2.35 (s, 3H), 3.75 (s, 3H), 4.55 (s, 2H), 6.7 (dd, J=12Hz, J=3Hz, 1H), 6.9 (d, J=9Hz,1H) 7.19 (d, J=3Hz, 1H), 7.40–7.45 (m, 2H), 7.6–7.75 (m, 4H), 7.95 (s, 1H), 8.0–8.15 (m, 1H), 8.2 (s, 1H), 8.45–8.55 (m, 1H); MS: (DCI) (M+H)$^+$ m/z=529. Anal. Calcd for $C_{29}H_{21}ClN_2O_2S_2$: C, 65.83; H, 4.00; N, 5.29. Found: C, 65.59; H, 4.05; N, 5.10.

Example 8

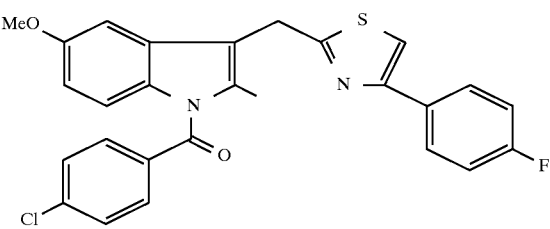

1-(4-Chlorobenzoyl)-3-[4-(4-fluorophenyl)thiazol-2-ylmethyl]-5-methoxy-2-methylindole.

The product was prepared according to the procedure for example 1 substituting 2-bromo-4'-fluoroacetophenone for 2,4'-dibromoacetophenone in step 3. m.p. 172°–174° C. $^1$H NMR (DMSO-$d_6$) δ: 2.35 (s, 3H), 3.75 (s, 3H), 4.5 (s, 2H), 6.7 (dd, J=12Hz, J=3Hz, 1H), 6.9 (d, J=9Hz, 1H) 7.19 (d, J=3Hz, 1H), 7.25 (t, J=9Hz, 2H), 7.6–7.75 (m, 4H), 7.8 (s, 1H), 7.95–8.0 (m, 2H); MS: (DCI) (M+H)$^+$ m/z=491. Anal. Calcd for $C_{27}H_{20}ClFN_2O_2S$: C, 66.05; H, 4.11; N, 5.71. Found: C, 66.18; H, 4.14; N, 5.48.

Example 9

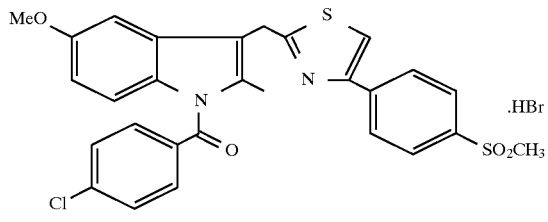

4-methanesulfonylacetophenone.

To 4-(methylthio)acetophenone (1.0 g; 6 mmol) in 20 mL CH$_2$Cl$_2$ was added mCPBA (3.1 g; 18 mmol). The reaction was stirred at r.t. for 2 hrs. The reaction was diluted with EtOAC and rinsed successively with sodium metabisulfite (2x), NaHCO$_3$ (2x), and brine. The extracts were dried over MgSO$_4$ and evaporated to give a white powder that was used with no further purification.

2-bromo-4'-methanesulfonylacetophenone.

To 4-methanesulfonylacetophenone (480 mg; 2.42 mmol) in 15 mL HOAC was added Br$_2$ (2.42 mmol). The reaction was stirred overnight at r.t. The reaction mixture was carefully poured into NaHCO$_3$ solution and extracted with EtOAC. The reaction yielded a light yellow solid which was used with no further purifiCation.

1-(4-Chlorobenzoyl)-3-[4-(4-methanesulfonylphenyl) thiazol-2-ylmethyl]-5-methoxy-2-methylindole hydrobromide salt.

The product was prepared according to the procedure for example 1 substituting 2-bromo-4'-methanesulfonylacetophenone for 2,4'-dibromoacetophenone in step 3. mp 125°–128° C. $^1$H NMR (DMSO-d$_6$) δ: 2.35 (s, 3H), 3.75 (s, 3H), 4.5 (s, 2H), 4.8 (bs) 6.7 (dd, J=12Hz, J=3Hz, 1H), 6.9 (d, J=9Hz, 1H) 7.19 (d, J=3Hz, 1H), 7.6–7.75 (m, 4H), 8.0 (d, J=9Hz, 2H), 8.2 (d, J=9Hz, 3H); MS: (DCI) (M+H)$^+$ m/z=551. Anal. Calcd for C$_{28}$H$_{23}$ClN$_2$O$_4$S$_2$·1.25HBr: C, 54.22; H, 3.94; N, 4.51. Found: C, 53.59; H, 3.68; N, 4.47.

Example 10

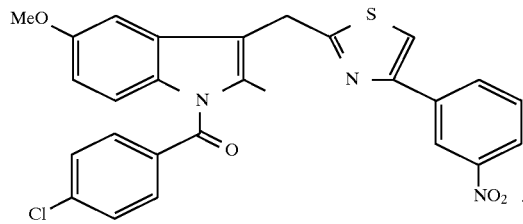

1-(4-Chlorobenzoyl)-5-methoxy-2-methyl-3-[4-(3-nitrophenyl)thiazol-2-ylmethyl]indole.

The product was prepared according to the procedure for example 1 substituting 2-bromo-3'-nitroacetophenone for 2,4'-dibromoacetophenone in step 3. m.p. 162°–164° C. $^1$H NMR (DMSO d$_6$) δ: 2.36 (s, 3H), 3.76 (s, 3H), 4.55 (s, 2H), 6.75 (dd, J=3Hz, J=10Hz, 1H), 6.98 (d, J=10Hz, 1H), 7.20 (d, J=3Hz, 1H), 7.6–7.8 (m, 5 H), 8.19–2.1 (m, 1H), 8.28 (s, 1H), 8.39–8.41 (m, 1H), 8.79–8.80 (m, 1H); MS: (DCI) (M+H)$^+$ m/z=518/520. Anal. Calcd for C$_{27}$H$_{20}$ClN$_3$O$_4$S: C, 62.60; H, 3.89; N, 8.11. Found: C, 62.41; H, 3.86; N, 7.95.

Example 11

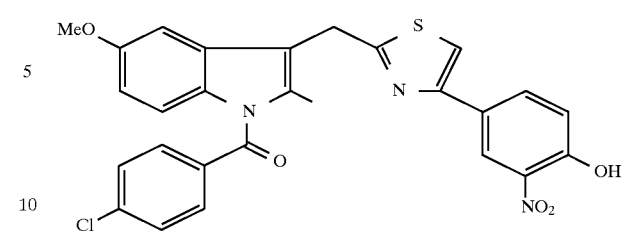

1-(4-Chlorobenzoyl)-3-[4-(4-hydroxy-3-nitrophenyl) thiazol-2-ylmethyl]-5-methoxy-2-methylindole.

The product was prepared according to the procedure for example 1 substituting 2-bromo-4'-hydroxy-3'-nitroacetophenone for 2,4'-dibromoacetophenone in step 3. m.p. 175°–177° C. $^1$H NMR (DMSO-d$_6$) δ: 2.35 (s, 3H), 3.75 (s, 3H), 4.5 (s, 2H), 4.8 (bs) 6.7 (dd, J=12Hz, J=3Hz, 1H), 6.9 (d, J=9Hz, 1H), 7.19–7.22 (m, 2H), 7.42 (s, 1H), 7.6–7.78 (m, 4H), 8.0 (s, 1H), 8.1 (dd, J=12Hz, J=3Hz, 1H), 8.5 (d, J=3Hz, 1H); MS: (DCI) (M+H)$^+$ m/z=534. Anal. Calcd for C$_{27}$H$_{20}$ClN$_3$O$_5$S: C, 60.73H, 3.78; N, 7.87. Found: C, 60.07; H, 4.03; N, 7.57.

Scheme II

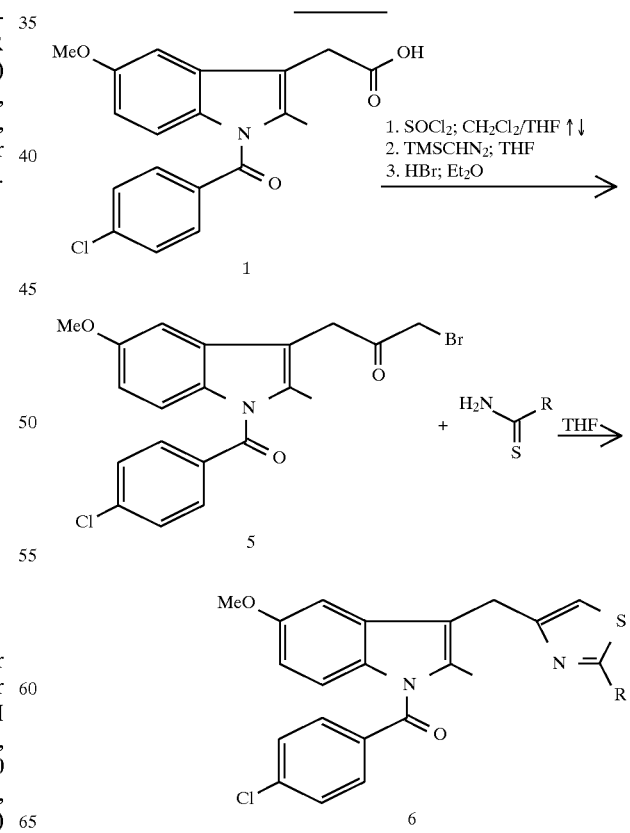

-continued
Scheme II

Example 12:

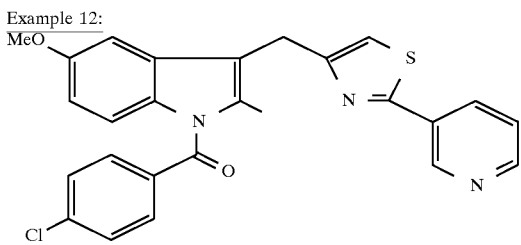

Step 1
3-(3-bromo-2-oxoprop-1-yl)-1-(4-Chlorobenzoyl)-5-methoxy-2-methylindole.

Indomethacin (8.9 g; 25 mmol) in 100 mL $CH_2Cl_2$ and 20 mL THF was treated with thionyl Chloride (14.7 g; 125 mmol) and heated at reflux for 3 hrs. The volatiles were removed under reduced pressure. The residue was dissolved in 30 mL THF and 25 mL trimethylsilyldiazomethane solution (2.0M in hexanes) was added dropwise. The reaction mixture was stirred at room temperature for 2 hrs. The volatiles were evaporated in vacuo and the residue was suspended in 50 mL $Et_2O$. The mixture was cooled in a water bath and 10 mL 48% HBr was added slowly. After 1 hr. at r.t. the mixture was stored overnight in the freezer. The mixture was allowed to warm to r.t. then diluted with water and extracted with EtOAC (2×). The extracts were rinsed successively with water (3×) and brine (1×), dried over $MgSO_4$ and evaporated. The product was isolated by flash chromatography (15–20% EtOAc/hexanes). The reaction yielded 5.6 g (52%) of a tacky brownish material.

Step 2
1-(4-Chlorobenzoyl)-5-methoxy-2-methyl-3-[2-(3-pyridyl)thiazol-4-ylmethyl]indole.

The bromomethylketone from step 1 (285 mg; 0.66 mmol) and thionicotinamide (91 mg; 0.66 mmol) in 10 mL THF were heated at reflux for 5 hrs. The solvent was evaporated and the product was isolated by flash chromatography (30% EtOAc/hexanes). The reaction yielded 110 mg (35%) of a yellow solid. $^1H$ NMR (DMSO-$d_6$) δ: 2.35 (s, 3H), 3.75 (s, 3H), 4.22 (s, 2H), 4.8 (bs) 6.7 (dd, J=12Hz, J=3Hz, 1H), 6.9 (d, J=9Hz, 1H), 7.19 (d, J=3Hz, 1H), 7.42 (s, 1H), 7.5–7.6 (m, 1H), 7.62–7.79 (m, 4H), 8.25–8.3 (m, 1H), 8.6 (dd, J=9Hz, J=3Hz, 1H), 9.05 (d, J=3Hz, 1H); MS: (DCI) (M+H)$^+$ m/z=474. Anal. Calcd for $C_{26}H_{20}ClN_3O_2S$: C, 65.88; H, 4.25; N, 8.86. Found: C, 65.42; H, 4.35; N, 8.25.

Example 13

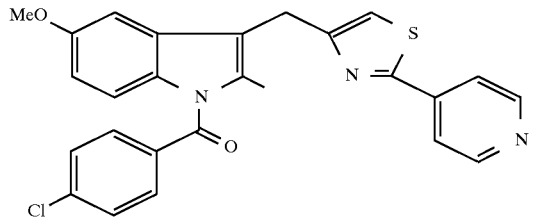

1-(4-Chlorobenzoyl)-5-methoxy-2-methyl-3-[2-(4-pyridyl)thiazol-4-ylmethyl]indole.

The product was prepared according to the procedure for example 12 substituting thioisonicotinamide for thionicotinamide in step 2. mp 109°–114° C. $^1H$ NMR (DMSO-$d_6$) δ: 2.35 (s, 3H), 3.75 (s, 3H), 4.22 (s, 2H), 4.8 (bs) 6.7 (dd, J=12Hz, J=3Hz, 1H), 6.9 (d, J=9Hz, 1H), 7.19 (d, J=3Hz, 1H), 7.55 (s, 1H), 7.6–7.7 (m, 4H), 8.8–8.85 (m, 2H), 8.6 (dd, J=9Hz, J=3Hz, 2H); MS: (DCI) (M+H)$^+$ m/z=474. Anal. Calcd for $C_{26}H_{20}ClN_3O_2S \cdot 0.25$ $H_2O$: C, 65.26; H, 4.31; N, 8.78. Found: C, 65.06; H, 4.22; N, 8.60.

Scheme III

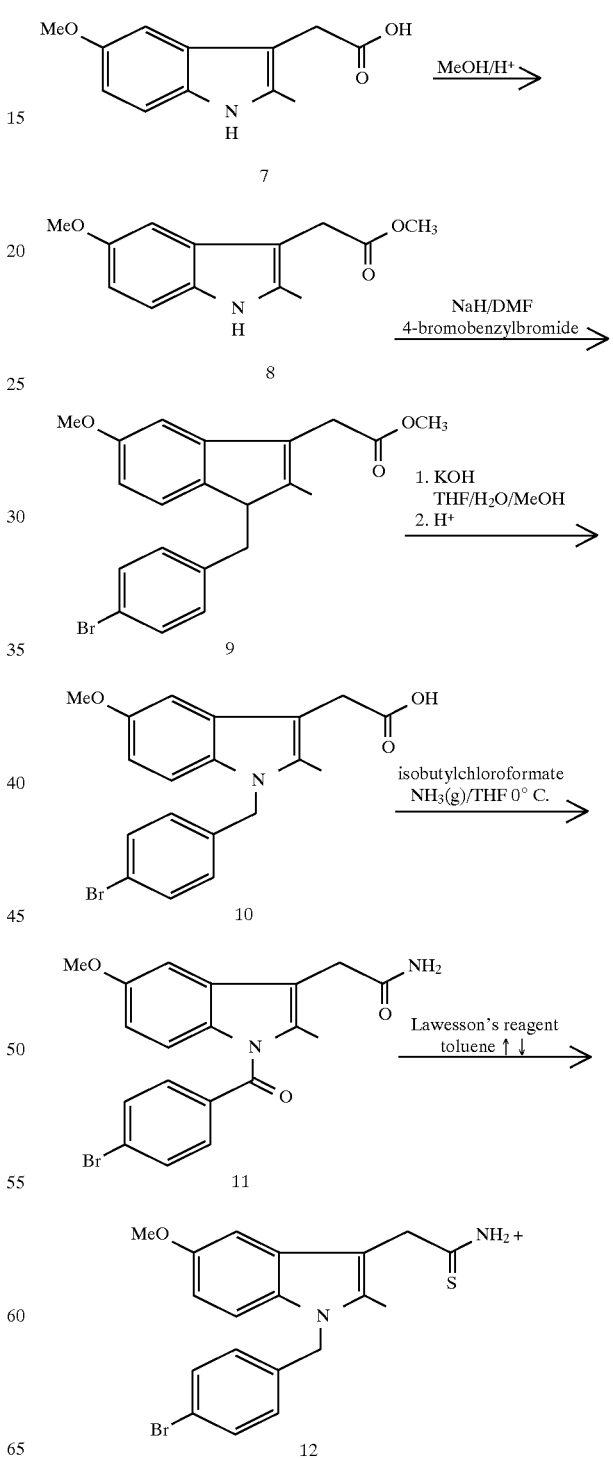

-continued
Scheme III

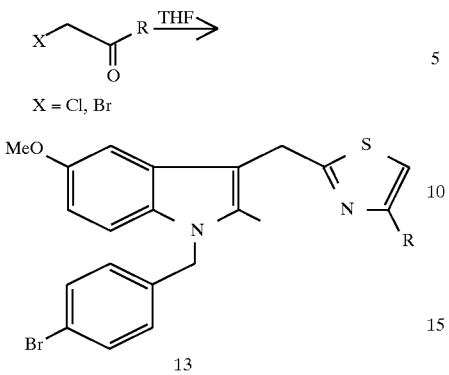

13

Example 14

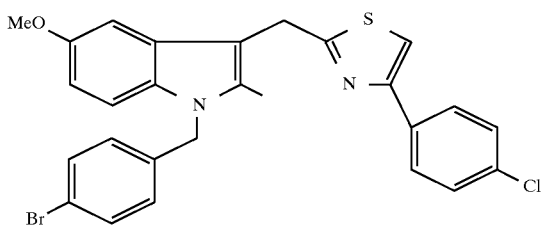

Step 1

Methyl 5-methoxy-2-methylindole-3-acetate.

To a solution of 5-methoxy-2-methylindole-3-acetic acid (10 g, 45.6 mmol) in 100 mL of methanol was added 10 drops of concentrated sulfuric acid. The reaction mixture was heated at reflux for 2 h then cooled to room temperature. The pH was adjusted to approximately or about 7 using 1N NaOH. The solvent was removed under reduced pressure. The yellow oily residue was dissolved in methylene Chloride and filtered through a plug of silica gel using 2% methanol/$CH_2Cl_2$. The solvent was removed to give 10.6 g (quantitative) of the methyl ester as a yellow oil.

Step 2

Methyl 1-(4-bromobenzyl)-5-methoxy-2-methylindole-3-acetate.

To a solution of 10.67 g (45.6 mmol) of methyl 5-methoxy-2-methylindole-3-acetate in 100 mL of DMF at 0° C. was added 2.07 g (50.2 mmol) sodium hydride (60% dispersion in mineral oil). The reaction mixture was stirred for 30 min. then 4-bromobenzyl bromide (13 g, 50.2 mmol) was added. After 1 h at 0° C., the reaction mixture was poured into 100 mL of saturated $NH_4Cl$. The mixture was extracted with $CH_2Cl_2$ (4×). The Combined organics were washed with $H_2O$ (3×) and brine (1×), dried over $Na_2SO_4$ and concentrated. The produCt (10 g; 54% yield) was isolated by flash chromatography (8:2:1 hexanes/$CH_2Cl_2$/EtOAC).

Step 3

1-(4-Bromobenzyl)-5-methoxy-2-methylindole-3-acetic acid.

A solution of methyl 1-(4-bromobenzyl)-5-methoxy-2-methylindole-3-acetate (10 g, 24.9 mmol) and KOH (1.7 g, 30 mmol) in 45 mL of THF, 5 mL of $H_2O$, and 2 mL of methanol was heated at reflux for 1 h. The reaction mixture was cooled to 0° C. and neutralized with concentrated HCl. The solvent volume was reduced by rotary evaporation. The precipitate was collected and washed with $H_2O$. The white solid was dried in a vacuum oven to give 9.5 g (98%) of the carboxylic acid.

Step 4

1-(4-Bromobenzyl)-5-methoxy-2-methylindole-3-acetamide.

To a solution of 1-(4-bromobenzyl)-5-methoxy-2-methylindole-3-acetic acid (8.5 g, 21.9 mmol) in 85 mL of THF at −10° C. was added triethylamine (3.8 mL, 27.4 mmol) and isobutylchloroformate (3.4 mL, 26.3 mmol). The reaction mixture was stirred for 15 min. then ammonia gas was bubbled through the solution for 5 min. A white precipitate formed whiCh was collected by vacuum filtration. The solid was washed with $H_2O$ then THF to give 6.8 g (80%) of the desired amide.

Step 5

1-(4-Bromobenzyl)-5-methoxy-2-methylindole-3-thioacetamide.

To a suspension of 1-(4-bromobenzyl)-5-methoxy-2-methylindole-3-acetamide (2 g, 5.16 mmol) in 75 mL of toluene was added 626 mg (1.55 mmol) of Lawesson's reagent. The reaction mixture was slowly warmed to reflux (Ca. 1 h) then cooled to room temperature. Silica gel was added, and the solvent was removed by rotary evaporation. The silica was added to the top of a flash chromatography column and eluted with 2% methanol/$CH_2Cl_2$ to give 1.79 g (86%) of the thioamide as a white solid.

Step 6

1-(4-bromobenzyl)-3- [4-(4-Chlorophenyl)thiazol-2-ylmethyl]-5-methoxy-2-methylindole.

To a solution of the 1-(4-bromobenzyl)-5-methoxy-2-methylindole-3-thioacetamide (200 mg, 500 mmol) in 5 mL of THF was added 2-bromo-4'-chloroacetophenone. After 10 min. a precipitate formed. The reaction mixture was heated at reflux for 30 min. then cooled to room temperature. The solid was collected by vacuum filtration and washed with 1:1 hexane/THF. The product was recrystallized from $CHCl_3$/methanol to give 196 mg (73%) of the 4-Chlorophenyl thiazole as white needles. m.p. 169°–170° C. $^1$H NMR ($d_6$-DMSO, 300 MHz) δ: 7.98 (d, J=8.5Hz, 2H), 7.93 (s, 1H), 7.49 (dd, J=8.6, J=2.0Hz, 4H), 7.28 (d, J=8.8Hz, 1H), 7.04 (d, J=2.6Hz, 1H), 6.90 (d, J=8.5Hz, 2H), 6.70 (dd, J=8.8Hz, J=2.2Hz, 1H), 5.40 (s, 2H), 4.45 (s, 2H), 3.71 (s, 3H), 2.33 (s, 3H); MS: (DCI) (M+H)$^+$ m/z=539. Anal. Calcd for $C_{27}H_{22}BrClN_2OS$: C, 60.29; H, 4.12; N, 5.12. Found: C, 59.92; H, 4.02; N, 5.05.

Example 15

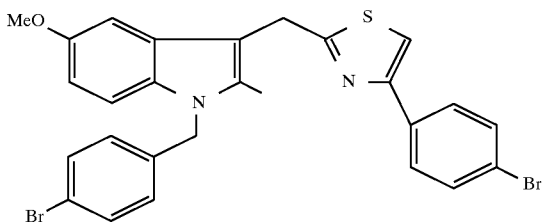

1-(4-bromobenzyl)-3-[4-(4-bromophenyl)thiazol-2-ylmethyl]-5-methoxy-2-methylindole.

The product was prepared according to the procedure for example 14 substituting 2,4'-dibromoacetophenone for 2-bromo-4'-chloroacetophenone in step 6. m.p. 178°–179° C. $^1$H NMR (d$_6$-DMSO, 300 MHz) δ: 7.95 (s, 1H), 7.92 (d, J=8.5Hz, 1H), 7.64 (d, J=8.5Hz, 1H), 7.48 (d, J=8.5Hz, 1H), 7.28 (d, J=8.8Hz, 1H), 7.04 (d, J=2.2Hz, 1H), 6.90 (d, J=8.5Hz, 1H), 6.69 (dd, J=8.8, J=2.6Hz, 1H), 5.4 (s, 2H), 4.45 (s, 2H), 3.71 (s, 3H), 2.33 (s, 3H); MS: (DCI) (M+H)$^+$ m/z=583. Anal. Calcd for C$_{27}$H$_{22}$Br$_2$N$_2$OS: C, 55.69; H, 3.81; N, 4.81. Found: C, 55.43; H, 3.88; N, 4.76.

Example 16

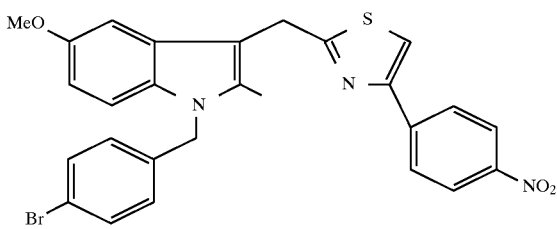

1-(4-bromobenzyl)-5-methoxy-2-methyl-3-[4-(4-nitrophenyl)thiazol-2-ylmethyl]indole.

The product was prepared according to the procedure for example 14 substituting 2-bromo-4'-nitroacetophenone for 2-bromo-4'-chloroacetophenone in step 6. m.p. 205°–207° C. $^1$H NMR (d$_6$-DMSO, 300 MHz) δ: 8.32 (d, J=9.3Hz, 2H), 8.25 (s, 1H), 8.23 (d, J=9.3Hz, 2H), 7.50 (d, J=8.5Hz, 1H), 7.30 (d, J=8.8Hz, 1H), 7.04 (d, J=2.2Hz, 1H), 6.90 (d, J=8.4Hz, 1H), 6.70 (dd, J=8.8, J=2.2Hz, 1H), 5.41 (s, 2H), 4.49 (s, 2H), 3.71 (s, 3H), 2.34 (s, 3H); MS: (DCI) (M+H)$^+$ m/z=550. Anal. Calcd for C$_{27}$HH$_{22}$BrN$_3$O$_3$S: C, 59.13; H, 4.04; N, 7.66. Found: C, 59.04; H, 3.83; N, 7.74.

What is claimed is:

1. A compound of the formula:

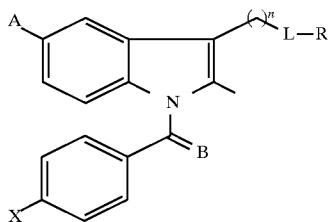

wherein,
A is selected from halogen, C$_1$–C$_6$alkyl, haloC$_1$–C$_4$alkyl, SR$^1$ or OR$^1$;
B is selected from O or H,H;
X is selected from Br or Cl;
L is thiazole;
n is selected from 1–6, wherein the carbon is optionally branched;
R is selected from
(a) unsubstituted or mono- or multi-substituted aryl wherein aryl is selected from phenyl or naphthyl and the substituents are independently selected from halogen (Cl, Br, or F); NO$_2$, OH, SO$_2$R$^2$ wherein R$^2$ is C$_1$–C$_6$alkyl; or
(b) unsubstituted or mono- or multi-substituted heteroaryl wherein heteroaryl is selected from pyridyl, benzothienyl, or quinoxolyl and the substituents are independently selected from halogen (Cl, Br, or F); NO$_2$, OH, SO$_2$R$^2$ wherein R$^2$ is C$_1$–C$_6$alkyl; and
R$^1$ is selected from C$_1$–C$_6$alkyl, or a pharmaceutically acceptable salt or prodrug thereof.

2. A compound according to claim 1 wherein A is selected from —OR$^1$ and X, B, L, R and n are as defined in claim 1.

3. A compound according to claim 1 wherein R is selected from unsubstituted or substituted phenyl, pyridyl, naphthyl, benzothienyl or quinoxolyl.

4. A compound according to claim 1 wherein A is chosen from —OR$^1$, wherein R$^1$ is C$_1$–C$_3$alkyl; B is selected from O or H,H; X is selected from Cl or Br; R is selected from p-Br-phenyl, difluorophenyl, naphthyl, m-Br-phenyl, p-Cl-phenyl, p-nitro-phenyl, benzothienyl, p-F-phenyl, p-SO$_2$CH$_3$,HCl-phenyl, m-nitro-phenyl, p-OH, m-nitro-phenyl, pyrid-3-yl, or pyrid-4-yl and n is chosen from 1.

5. A compound selected from,
3-(4-(4-bromophenyl)thiazol-2-ylmethyl)-1-(4-Chlorobenzoyl)-5-methoxy-2-methylindole;
1-(4-Chlorobenzoyl)-3-[4-(2,4-difluorophenyl)thiazol-2-ylmethyl]-5-methoxy-2-methylindole;
1-(4-Chlorobenzoyl)-5-methoxy-2-methyl-3-[4-(2-naphthyl)thiazol-2-ylmethyl]indole;
3-[4-(3-bromophenyl)thiazol-2-ylmethyl]1-(4-Chlorobenzoyl)-5-methoxy-2-methylindole;
1-(4-Chlorobenzoyl)-3-[4-(4-Chlorophenyl)thiazol-2-ylmethyl]-5-methoxy-2-methylindole;
1-(4-Chlorobenzoyl)-5-methoxy-2-methyl-3-[4-(4-nitrophenyl)thiazol-2-ylmethyl]indole;
3-[4-(3-benzothienyl)thiazol-2-ylmethyl]-1-(4-Chlorobenzoyl)-5-methoxy-2-methylindole;
1-(4-Chlorobenzoyl)-3-[4-(4-fluorophenyl)thiazol-2-ylmethyl]-5-methoxy-2-methylindole;
1-(4-Chlorobenzoyl)-3-[4-(4-methanesulfonylphenyl)thiazol-2-ylmethyl]-5-methoxy-2-methylindole hydrobromide salt;
1-(4-Chlorobenzoyl)-5-methoxy-2-methyl-3-[4-(3-nitrophenyl)thiazol-2-ylmethyl]indole;
1-(4-Chlorobenzoyl)-3-[4-(4-hydroxy-3-nitrophenyl)thiazol-2-ylmethyl]-5-methoxy-2-methylindole;
1-(4-Chlorobenzoyl)-5-methoxy-2-methyl-3-[2-(3-pyridyl)thiazol-4-ylmethyl]indole;
1-(4-Chlorobenzoyl)-5-methoxy-2-methyl-3-[2-(4-pyridyl)thiazol-4-ylmethyl]indole;
1-(4-bromobenzyl)-3-[4-(4-Chlorophenyl)thiazol-2-ylmethyl]-5-methoxy-2-methylindole;
1-(4-bromobenzyl)-3-[4-(4-bromophenyl)thiazol-2-ylmethyl]-5-methoxy-2-methylindole; or 1-(4-bromobenzyl)-5-methoxy-2-methyl-3-[4-(4-nitrophenyl)thiazol-2-ylmethyl]indole.

6. A pharmaceutical composition comprising a compound according to claim 1 and a pharmaceutically acceptable carrier.

7. A method of inhibiting a PGHS-2 isozyme in mammals comprising administering an inhibitory effective amount of a compound according to claim 1 to a mammal.

* * * * *